(12) United States Patent
Di Scalea et al.

(10) Patent No.: US 8,626,459 B2
(45) Date of Patent: Jan. 7, 2014

(54) DEFECT DETECTION IN OBJECTS USING STATISTICAL APPROACHES

(75) Inventors: Francesco Lanza Di Scalea, San Diego, CA (US); Stefano Coccia, Los Angeles, CA (US); Ivan Bartoli, Philadelphia, PA (US); Salvatore Salamone, Buffalo, NY (US); Piervincenzo Rizzo, Pittsburgh, PA (US)

(73) Assignee: The Regents of the University of California, Oakland, CA (US)

( * ) Notice: Subject to any disclaimer, the term of this patent is extended or adjusted under 35 U.S.C. 154(b) by 322 days.

(21) Appl. No.: 13/121,092

(22) PCT Filed: Sep. 25, 2009

(86) PCT No.: PCT/US2009/058442
§ 371 (c)(1),
(2), (4) Date: Jun. 13, 2011

(87) PCT Pub. No.: WO2010/036934
PCT Pub. Date: Apr. 1, 2010

(65) Prior Publication Data
US 2011/0238336 A1  Sep. 29, 2011

Related U.S. Application Data

(60) Provisional application No. 61/100,239, filed on Sep. 25, 2008.

(51) Int. Cl.
*G06F 17/18* (2006.01)
(52) U.S. Cl.
USPC ............ 702/56; 702/34; 702/51; 702/76; 73/600; 73/628; 73/865.8
(58) Field of Classification Search
USPC ............ 702/34, 76, 51, 56; 73/597, 600, 628, 73/865.8, 593, 602, 40.5 A, 12.08, 12.09, 73/598, 636, 632, 592, 668
See application file for complete search history.

(56) References Cited

U.S. PATENT DOCUMENTS 4,174,636 A * 11/1979 Pagano ........................ 73/636
4,330,728 A * 5/1982 Solie ........................ 310/313 B
(Continued)

FOREIGN PATENT DOCUMENTS

| JP | 2002-195987 A | 7/2002 |
|---|---|---|
| JP | 2006-220569 A | 8/2006 |
| JP | 2008-107165 A | 5/2008 |

OTHER PUBLICATIONS

Rizzo, et al., "Wavelet-based outlier analysis for guided wave structural monitoring: Application to multi-wire strands", J. Sound and Vibration, 2007, vol. 307, pp. 52-68.

(Continued)

*Primary Examiner* — Carol S Tsai
(74) *Attorney, Agent, or Firm* — Mintz Levin Cohn Ferris Glovsky and Popeo, P.C.

(57) ABSTRACT

Disclosed are systems, methods and articles, including an inspection system that includes at least one generator to apply energy to an object at an application point to cause waves to travel, at least partly, through the object. The system further includes at least one detector configured to detect at least a portion of the waves traveling through the object, and a statistical analyzer to perform a statistical analysis based on an output produced by the at least one detector in response to the detected portion of the waves, the statistical analysis being used to determine whether at least one defect is present in the object.

32 Claims, 8 Drawing Sheets

(56) References Cited

U.S. PATENT DOCUMENTS

| | | | |
|---|---|---|---|
| 4,603,584 A * | 8/1986 | Bartle et al. | 73/599 |
| 5,600,133 A * | 2/1997 | Spillman, Jr. | 250/227.14 |
| 6,055,862 A * | 5/2000 | Martens | 73/632 |
| 6,186,004 B1 | 2/2001 | Kaduchak et al. | |
| 6,401,044 B1 | 6/2002 | Ibanez et al. | |
| 6,895,358 B2 * | 5/2005 | Besserer et al. | 702/159 |
| 7,082,833 B2 * | 8/2006 | Heyman et al. | 73/598 |
| 7,516,662 B2 * | 4/2009 | Nielsen et al. | 73/598 |
| 7,526,959 B2 * | 5/2009 | Kim et al. | 73/628 |
| 7,882,742 B1 * | 2/2011 | Martens | 73/636 |
| 8,201,453 B2 * | 6/2012 | Kondo | 73/600 |
| 2002/0148931 A1 * | 10/2002 | Anderson | 246/121 |
| 2004/0003662 A1 | 1/2004 | Kenderian et al. | |
| 2004/0105608 A1 * | 6/2004 | Sloman | 385/12 |
| 2006/0201253 A1 | 9/2006 | Gonzales et al. | |
| 2006/0287836 A1 | 12/2006 | Martinez | |
| 2007/0163352 A1 * | 7/2007 | Nielsen et al. | 73/668 |
| 2010/0024559 A1 | 2/2010 | Bossi et al. | |

OTHER PUBLICATIONS

PCT International Search Report dated Jul. 18, 2013 for PCT application No. PCT/US2013/034977.

\* cited by examiner

DEFECT DETECTION IN OBJECTS USING STATISTICAL APPROACHES

CROSS REFERENCE TO RELATED APPLICATION

This application is a national stage application, filed under 35 U.S.C. §371, of International Application No. PCT/US2009/058442, filed on Sep. 25, 2009, which claims the benefit of, and priority to, U.S. Provisional Patent Application Ser. No. 61/100,239, entitled "ULTRASONIC SYSTEM FOR THE INSPECTION OF RAILROAD TRACKS", filed Sep. 25, 2008, the content of both applications are hereby incorporated by reference in their entirety.

STATEMENT OF GOVERNMENT SPONSORED SUPPORT

This invention was made with government support under grant No. DTFR53-02-G-0001 awarded by Federal Railroad Administration (FRA). The government has certain rights in the invention.

BACKGROUND

The present disclosure is directed to defect detection in objects, and more particularly to defect detection using statistical analyses and procedures performed on output responsive to detected portions of waves (e.g., acoustic waves) traveling in the objects.

Conventional rail inspection techniques rely on the use of electromagnetic (EM) induction testing, or ultrasonic testing (UT) inspection, and the processing of acquired data generally using non-statistical techniques. Examples of non-statistical techniques used to inspect rails are those of ultrasonic pulse-echo or through-transmission testing, in which a defect is detected by the appearance of an ultrasonic echo (pulse-echo) or a drop in ultrasonic amplitude (through-transmission). Such analysis relies on one individual signal, without any statistical analysis. These analyses are therefore deterministic, i.e. they are affected by the inherent signal variability due to realistic environmental and operational conditions which greatly limits the reliability of defect detection achievable. The use of EM and UT techniques together with the processing of acquired data using non-statistical analysis procedures often leads to occurrences of both "false positives" (e.g., undamaged regions of the object, such as a rail, being erroneously flagged as cracked), and "false negatives" (e.g., defects that are not detected). False negatives are of particular concern because failure to detect defects in rail tracks may lead to train derailments. For example, the above inspection techniques have traditionally had difficulties in detecting internal cracks that are located under a subsurface discontinuity known as shelling (FIG. 1A). The latter type of defect was determined to be responsible, for example, for two major derailments in Superior, Wis., in 1991, and Hatfield, UK, in 2000.

Transverse cracks in the railhead are considered to be amongst the most serious defects found in rails, and are deemed to have been responsible for 541 derailments and $91 Million in direct cost during the period 1992-2002 in the US according to Federal Railroad Administration Safety Statistics. The associated indirect cost of these accidents is even higher. Other defects in rail are challenging to detect by conventional non-statistic inspections. These include vertical split head defects, horizontal split head defects, vertical split web defects, weld defects, and bolt hole cracks, as shown in FIG. 1B.

Another drawback of conventional inspection techniques, when applied to objects such as rails, is the relatively slow speed at which the inspection techniques can be performed. Typical inspection speed of rails, for example, using conventional systems/techniques is less than 20 miles per hour (mph).

SUMMARY

The subject matter disclosed herein relates to inspection systems (or apparatus), methods and articles that use statistical-based analysis to determine whether defects are present in the inspected object. In some embodiments, the systems, methods and articles described herein are applied to railroad tracks to identify defects (e.g., cracks) in rails.

The current subject matter of the present disclosure provides advantages in the use of statistical-based analysis with various ultrasonic generation and detection techniques by improving the reliability of detection of defects (including transverse cracks), by minimizing false positive indications and by improving the speed of inspection to faster than 40 mph.

In some embodiments, a statistical analysis based on an outlier analysis, discordancy test, or anomaly detection, such as Mahalanobis Squared Distance (M.S.D.), is performed. M.S.D. data points, computed based on feature values derived from outputs produced by one or more detectors, are compared to a corresponding baseline of features values derived using a similar system configuration applied on an undamaged portion of the inspected object which records the "normal" or baseline condition of the object. The metric computed by such a comparison may be classified as a defect if its value exceeds a pre-determined threshold, which is usually chosen to exceed a certain level of statistical confidence that a current feature value (or vector) is outside the baseline distribution. This statistical framework significantly reduces the number of false positives (i.e., undamaged rail locations being erroneously flagged as cracked), and the number of false negative (i.e., actual defects that are not detected), which ultimately increases the reliability of defect detection. Other statistical-based analysis procedures that may be used include Principal Component Analysis, Factor Analysis, Cluster Analysis, Linear Discriminant Analysis, etc.

In some embodiments, rail inspection may be performed by either contact-based ultrasonic testing (operated by water-filled wheels or dry-contact sleds) or non-contact inspection, performed, for example, using magnetic induction testing, eddy current, lasers, or air-coupled techniques. In some implementations, inspection apparatus (systems) generate waves (e.g., acoustic waves) in the objects and detect portions of the waves (ultrasonic bulk waves, such as Longitudinal or Shear Waves, or ultrasonic guided waves, such as Rayleigh waves). Outputs at the one or more detectors that is responsive to the detected guided waves portions are then analyzed using real-time, or near real-time, statistical processing of the measurements to thus improve the detection reliability/sensitivity of defects in the rail. These outputs may be generated by either a pulse-echo or a pitch-catch configuration of ultrasonic transducers using either ultrasonic bulk waves (e.g. longitudinal waves or shear waves) or ultrasonic guided waves (e.g. Rayleigh waves).

Real-time, or near real-time, statistical analysis of the detected signals is a breakthrough in ultrasonic rail inspections, and provides a substantial enhancement to defect detection performance by significantly decreasing the number of both false positive and false negative indications thus improving the overall reliability of defect detection.

In some implementations, the defect sensitivity provided by the statistical framework described herein exceeds that obtainable by non-statistical-based procedures by, for example, two orders of magnitude. This results in a significant increase in the reliability of the inspection apparatus, systems, methods and articles.

In some implementations, the use of ultrasonic waves traveling along, rather than across the rail section (ultrasonic guided waves), provides one or more of the following advantages: it increases the inspection speed from about 15 mph to over 40 mph; it is well-suited for detecting transverse head cracks (e.g., because the guided waves hit transverse crack perpendicularly (or near-perpendicularly), thus improving the likelihood of detecting transverse cracks, and can also travel underneath shellings and thus circumvent the inability of current inspections to detect internal defects under shelling.

In one aspect, an inspection system is disclosed. The system includes at least one generator to apply energy to an object at an application point to cause waves to travel, at least partly, through the object. The system further includes at least one detector configured to detect at least a portion of the waves traveling through the object, and a statistical analyzer to perform a statistical analysis based on an output produced by the at least one detector in response to the detected portion of the waves, the statistical analysis being used to determine whether at least one defect is present in the object.

Embodiments of the system may include any of the following features.

The statistical analyzer configured to perform the statistical analysis may be configured to perform on the output of the at least one detector one or more of, for example, an outlier analysis, a discordancy test and/or an anomaly detection.

The statistical analyzer configured to perform one or more of the outlier analysis, the discordancy test and/or the anomaly detection may be configured to compute one or more variation values between feature values of the detected portion of the waves and corresponding baseline feature values computed for a defect-free section of a representative object having a profile approximately similar to the profile of the inspected object.

The feature values may include one or more of, for example, root-mean square of an amplitude of the detected portion of the waves, variance of the amplitude of the detected portion of the waves, cross-correlation value of the amplitude of the detected portion of the waves, auto-correlation value of the amplitude of the detected portion of the waves, peak-to-peak value of the amplitude of the detected portion of the waves, peak value of the amplitude of the detected portion of the waves, Kurtosis value of the amplitude of the detected portion of the waves, at least one other time-domain Statistical Moment corresponding to properties of the detected portion of the waves, at least one other frequency-domain Statistical Moment corresponding to the properties of the detected portion of the waves and/or normalized values of any of the feature values.

The statistical analyzer configured to compute the one or more variation values between feature values of the detected portion of the waves and the corresponding baseline feature values may be configured to compute a value based on the equation Mahalanobis Squared Distance (M.S.D.)=$(x-\bar{x})^T \times Cov^{-1} \times (x-\bar{x})$, where x is a vector of the computed feature values, $\bar{x}$ is the mean vector of the corresponding baseline feature values, $C_{ov}$ represents a covariance matrix operation, $^T$ represents a transpose operation and $^{-1}$ represents an inverse matrix operation.

The statistical analyzer may further be configured to record computed M.S.D. values as a function of a moving application point.

The statistical analyzer may further be configured to record computed discordancy test values as a function of a moving application point.

The statistical analyzer may further be configured to record computed anomaly detection values as a function of a moving application point.

The at least one generator to apply energy to the object may be configured to apply energy to cause acoustic bulk waves, including one or more of longitudinal waves and shear waves, to travel through the object at specified angles to enhance the defect detection sensitivity.

The at least one detector may be configured to detect the portion of the waves within a pre-determined time window.

The statistical analyzer to perform the statistical analysis may be configured to determine one or more variation values between features of respective portions of bulk waves detected by the at least one detector.

The system may further include at least one device configured to act as the generator and the detector.

The at least one generator to apply energy may be configured to apply energy to cause acoustic waves having one or more components with corresponding frequencies to travel through the object to enhance the defect detection sensitivity at one or more object depths.

The at least one detector may include two or more acoustic detectors positioned at one of, for example, different sides of the application point and/or on the same side of the application point.

The two or more acoustic detectors may be configured to detect guided waves portions resulting from the energy applied to the object, the guided waves portions traveling at a direction substantially parallel to the longitudinal axis of the object.

The statistical analyzer to perform the statistical analysis may be configured to determine one or more variation values between features of the respective portions of the guided waves detected by the two or more detectors.

The statistical analyzer configured to compute the one or more variation values between features of the respective portions of the guided waves may be configured to compute ratio values of the features of the respective detected portions of the guided waves.

The object may include a rail of a railroad track, and the at least one defect may include an internal crack in the rail.

The generator may include one or more of, for example, an ultrasonic wheel generator, an ultrasonic sled generator, a water-coupled generator, a laser acoustic device, air-coupled transducer, an electro-magnetic acoustic transducer (EMAT) and/or a mechanical impactor.

The at least one generator may include the at least one detector.

The at least one generator to apply energy at the application point to cause acoustic waves to travel through the object may be configured to apply energy to the object at a moving application point.

In another aspect, a method is disclosed. The method includes applying energy to an object at an application point to cause resultant waves to travel, at least partly, through the object, detecting at least a portion of the waves traveling through the object, and performing a statistical analysis based on output produced in response to the detected portion of the waves, the statistical analysis being used to determine whether at least one defect is present in the object.

Embodiments of the method may include one or more of the above-described features of the system, as well as any of the following features.

Performing the statistical analysis may include performing one or more of, for example, an outlier analysis of the output produced in response to the detected portion of the waves, a discrepancy test of the output produced in response to the detected portion of the waves and/or an anomaly detection of the output produced in response to the detected portion of the waves.

Performing the one or more of the outlier analysis, the discrepancy test and the anomaly detection may include computing one or more variation values between feature values of the detected portion of the waves and corresponding baseline feature values computed for a defect-free section of a representative object having a profile approximately similar to a profile of the object having the energy applied to at the application point.

Computing one or more variation values may include computing a value based on the equation Mahalanobis Squared Distance $(M.S.D.) = (x-\bar{x})^T \times Cov^{-1} \times (x-\bar{x})$, where x is a vector of the computed feature values, $\bar{x}$ is the mean vector of the corresponding baseline feature values, coy represents a covariance matrix operation, $^T$ represents a transpose operation and $^{-1}$ represents an inverse matrix operation.

Applying energy to the object may include applying energy to cause acoustic bulk waves, including one or more of longitudinal waves and shear waves, to travel through the object at specified angles to enhance the defect detection sensitivity.

Applying energy to the object may include applying energy to cause acoustic waves having one or more components with corresponding frequencies to travel through the object to enhance the defect detection sensitivity at one or more object depths.

Detecting the portion of the waves may include detecting portions of the waves by two or more detectors positioned at one of, for example, different sides of the application point and/or on the same side of the application point.

In a further aspect, a computer program product residing on a computer readable medium is disclosed. The computer program product includes computer instructions that when executed on a processor-based device cause the processor-based device to perform a statistical analysis based on output produced in response to detected at least a portion of waves traveling through an object, the statistical analysis being used to determine whether at least one defect is present in the object, the waves are produced by applying energy to the object at an application point.

Embodiments of the computer program product may include one or more of the above-described features of the system and the method, as well as any of the following features.

The instructions that cause the processor-based device to perform the statistical analysis comprise instructions that cause the processor-based device to perform one or more of, for example, an outlier analysis of the output produced in response to the detected portion of the waves, a discrepancy test of the output produced in response to the detected portion of the waves, and an anomaly detection of the output produced in response to the detected portion of the waves.

The instructions that cause to processor-based device to perform the one or more of the outlier analysis, the discrepancy test and the anomaly detection may include instructions that cause the processor-based device to compute one or more variation values between feature values of the detected portion of the waves and corresponding baseline feature values computed for a defect-free section of a representative object having a profile approximately similar to a profile of the object having the energy applied to at the application point.

The instructions that cause the processor-based device to compute the one or more variation values may include instructions that cause the processor-based device to compute a value based on the equation Mahalanobis Squared Distance $(M.S.D.) = (x-\bar{x})^T \times Cov^{-1} \times (x-\bar{x})$, where x is a vector of the computed feature values, $\bar{x}$ is the mean vector of the corresponding baseline feature values, coy represents a covariance matrix operation, $^T$ represents a transpose operation and $^{-1}$ represents an inverse matrix operation.

The instructions further include instructions to cause the processor-based device to cause the energy to be applied to the object to cause acoustic bulk waves, including one or more of longitudinal waves and shear waves, to travel through the object at specified angles to enhance the defect detection sensitivity.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWING

These and other aspects will now be described in detail with reference to the following drawings.

Like reference symbols in the various drawings indicate like elements.

DETAILED DESCRIPTION

Figure 1A:
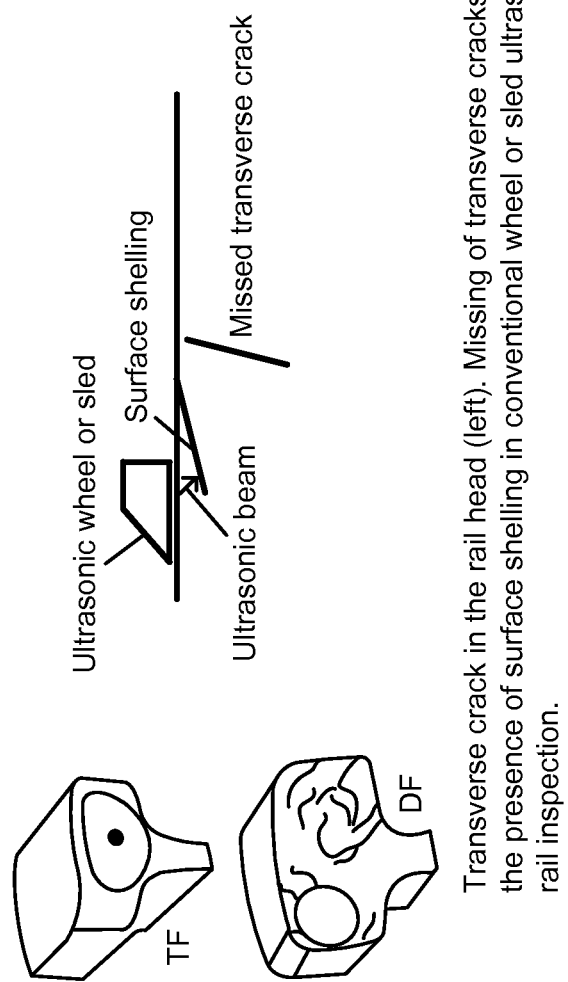
FIG. 1A is a view of an example rail head object.

Disclosed are systems, methods and articles, including an inspection system that includes at least one generator to apply energy to an object (e.g., a solid object such as a rail) at an application point to cause resultant waves (such as acoustic waves, or EM waves, e.g., X-rays) to travel, at least partly, through the object. The system also includes at least one detector configured to detect at least a portion of the waves traveling (or passing) through the object, and a statistical analyzer to perform a statistical analysis based on output produced by the at least one detector in response to the detected portion of the waves. The statistical analysis is used to determine whether at least one defect is present in the object. In some embodiments, the statistical analyzer may perform an outlier analysis (univariate or multivariate, etc.), a discordancy test and/or an anomaly detection to enable detection of anomalous statistical behavior (i.e., behavior that is deemed to be unusual compared to "normal" behavior, and thus deemed to be outlying behavior) that is indicative of a likely presence of a defect at the location at which such behavior has been identified.

In some embodiments, the object to which radiation is applied is a rail of a rail-track and the defect to be detected is an internal crack in the rail. Application of energy to the rail causes waves, e.g., ultrasonic waves, to be excited in the rail. The at least one detector detects at least a portion of the excited waves. In some embodiments, representative features computed (derived) from the detected portion of the waves may be compared, e.g., via a statistical analysis, to baseline feature values computed from detected waves in a defect-free portion of rail having a similar profile to the profile of the rail being inspected. Based on the resultant metric(s) computed from the analysis, which is representative of the comparison of the feature values, a determination can be made as to whether there is a defect in the object being inspected.

The present disclosure herein may thus be used to detect surface and/or internal cracks in the various sections of rails of railroad tracks (e.g., in the rail's head, web and base). In some implementations, the energy applied to the rail causes ultrasonic guided waves to travel (propagate) in the rail, and the guided waves may be detected at two or more locations (e.g., using two or more ultrasonic wave detectors). Ultrasonic guided waves are waves traveling along a rail's running direction (e.g., in a direction that is substantially parallel to the longitudinal axis of the rail), and can thus detect transverse cracks despite the presence of surface inhomogeneities (e.g., shelling) at sustained speeds (e.g., 15 mph, 40 mph, 100 mph, and/or faster or slower speeds). In some embodiments, the detectors are configured to detect other portions of ultrasonic waves excited in the object, for example, bulk waves (longitudinal waves and/or shear waves). In some implementations, the particular type of wave detected may be controlled by controlling the time window during which the detectors detect waves. For example, the detectors can be configured so that a relatively early time window (from the point at which the waves traveling in the object have been excited) is activated to thus detect specific types of waves. A more delayed time window may, on the other hand, result in the detection of other types of waves. Output produced by such detectors in response to the detected at least the portion of the waves (be it guided waves, bulk waves, or any type of wave) may then be analyzed by the statistical analyzer performing, for example, an outlier analysis, or by performing some other signal processing procedure, in which a current reading is compared to the "normal" (baseline) statistical distribution of a similar reading in a typical rail object.

The statistical analysis of the systems, apparatus, methods and articles described herein may be performed in a univariate or multivariate sense where at least one, and possibly multiple features (e.g., 2, 10, or more features) computed from the detected waves are arranged in a "feature vector." The "feature vector" is then statistically compared to a collection of "baseline vectors" representing a distribution of "normal" conditions of the rail through, for example, an outlier analysis, discordancy test or anomaly detection such as using a "Mahalanobis Squared Distance" procedure. If the metrics of the "Mahalanobis Distance" falls beyond a pre-determined threshold, the current "feature vector" is flagged as indicating a defected location; otherwise, it is flagged as indicating a defect-free location.

Figure 1B:
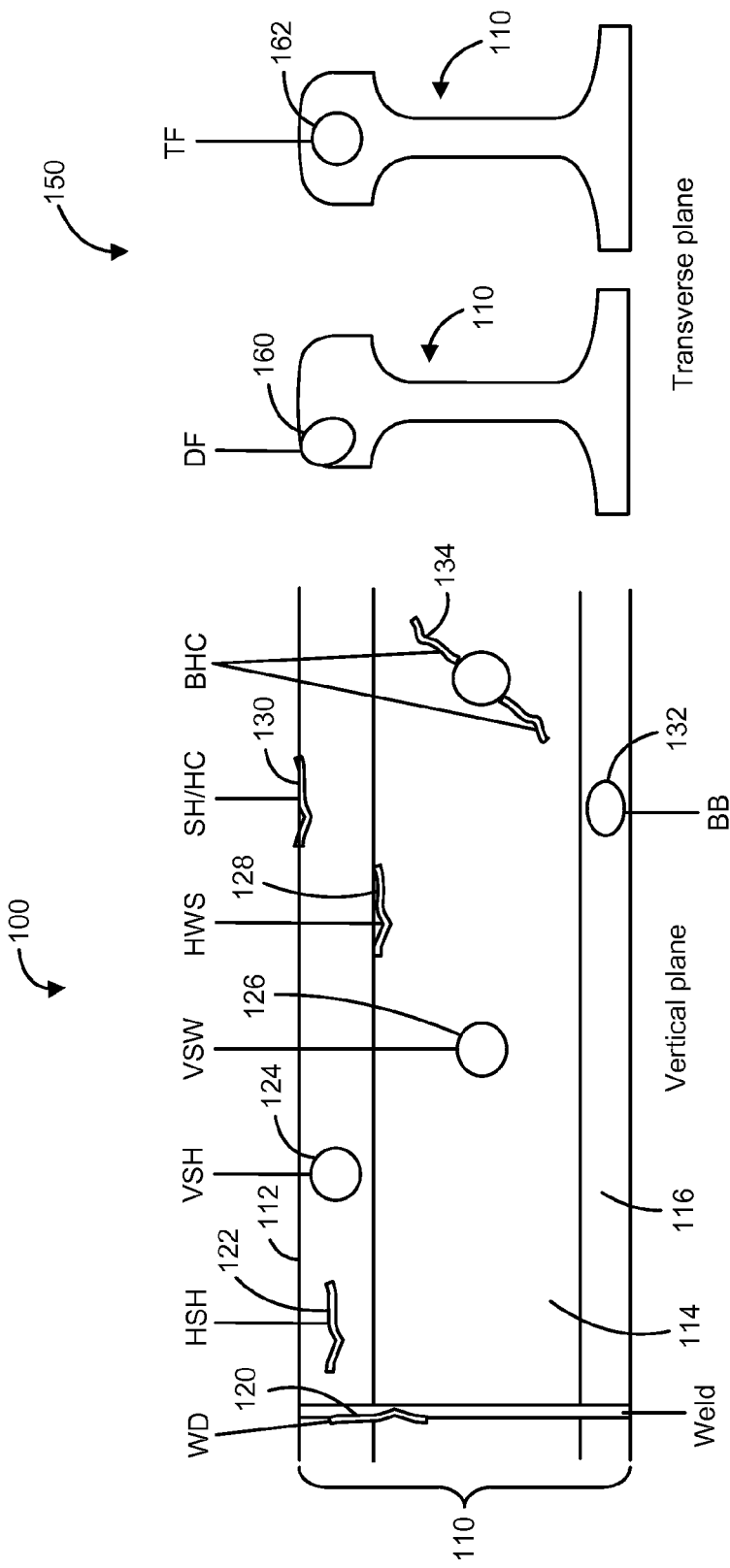
FIG. 1B shows two cross-section profiles of a section of a rail object with various types of defect illustrated therein.

With reference to FIG. 1B, cross-section diagrams illustrating various defects that may occur in an object such as a rail are shown. A diagram 100 shows some typical defects that can occur in a rail. The defects of diagram 100 are depicted in the vertical plane (e.g., along the longitudinal axis of a rail 110). The rail 110 includes a head section 112, a web section 114, and a base section 116. As shown, the various defect appearing in the diagram 100 include a weld defect (WD) 120, a horizontal split head (HSH) 122, a vertical split head (VSH) 124, a vertical split web (VSW) 126, a head-web separation (HWS) 128, a shelling/head checks (SH/HC) 130, a broken base (BB) 132, and a bolt hole cracks (BHC) 134. A diagram 150 shows some additional typical defects that can occur in a rail. The defects of diagram 150 are depicted in the transverse plane of the rail 110, and include a detail fracture (DF) 160, and a transverse fissure (TF) 162.

Figure 2A:
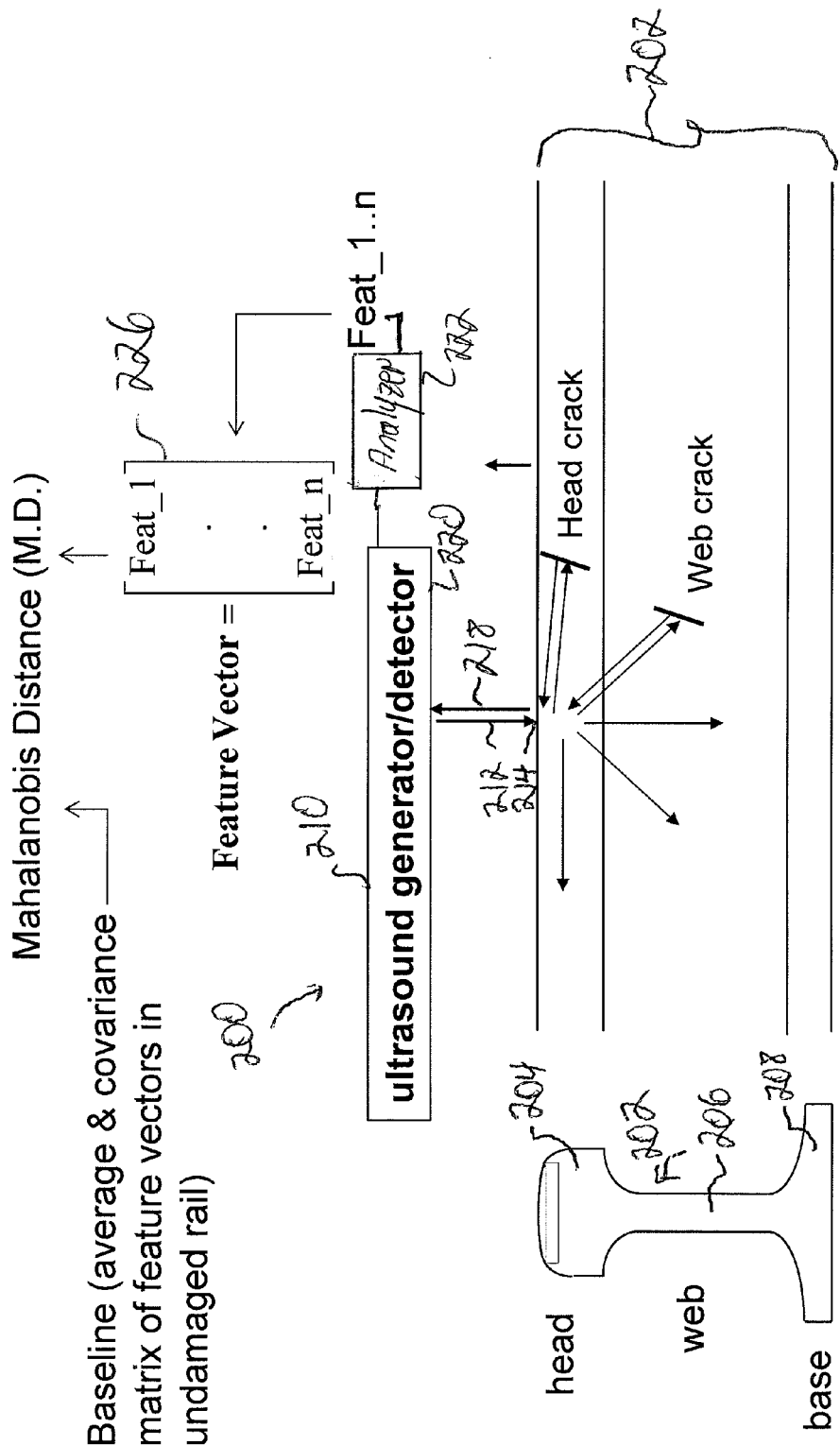
FIG. 2A is a schematic diagram of an example of an inspection system in a pulse-echo configuration (e.g., same device for the generator and detector)

Referring to FIG. 2A, a schematic diagram of an inspection system 200 is shown. For the purpose of illustration, an object 202 that is being inspected in FIG. 2A is a rail of railroad track (shown in cross-section) which includes a head 204, a web 206, and a base 208. However, the systems depicted in FIGS. 2A-C, and the methods implemented using, for example, the systems of FIGS. 2A-C, may similarly be used to inspect any other type of object to determine, for example, whether such objects have some defect therein (e.g., internal cracks). As shown, the system 200 includes at least one generator 210 to apply energy (depicted as an arrow 212) that is applied at an application point 214 on the object 202 (in FIG. 2A, the rail is also shown in a cross-section along the rail's longitudinal axis). The energy applied may be in the form of radiation energy (e.g., laser energy where a laser acoustic generator is used), acoustic wave energy (e.g., where a piezoelectric ultrasonic transducer that emits ultrasonic waves is used), or electromagnetic energy (e.g. an electromagnetic-acoustic transducer or EMAT), or mechanical energy (e.g. an impactor). In some implementations where the dimensions of the object are such that multiple measurements are required (e.g., for a long rail of a railroad track that may be extending over hundred or thousands of miles), the generator 210 may be mounted or fitted on some moving structure (for example, a moving platform towed by a locomotive). Under those circumstances, the generator 210 applies energy to the object at a moving application point 214. The moving application point may be moving at a speed matching, for example, the speed of the locomotive or slower.

The generator 210 applies energy 212 that, when applied to the object at the application point 214, causes, or excites, resulting waves to pass, or travel, at least partly, through the object 202. In some implementations, the generator 210 is an ultrasonic generator to cause ultrasonic waves to travel through the object 202. The generator 210 may be a contact generator, in which the generator is mechanically coupled to the object 202 (e.g., via a coupling layer such as a suitable fluid couplant, e.g. water), and causes resultant waves (acoustic waves) through mechanical excitation. Suitable contact-based generators may include, for example, an ultrasonic wheel generator (i.e., a moveable generator displaced over the object), an ultrasonic sled generator, and/or a water-coupled generator. These types of generators may include an ultrasonic transducer implemented, for example, using a piezoelectric element, or some other vibrating transducer, that mechanically oscillates at frequencies controllable by regulating the voltage/current applied to the piezoelectric element. In such implementations, the energy applied to the object is in the form of acoustic (ultrasonic) waves.

In some implementations, the generator 210 may be a non-contact generator, i.e., the generator is not in direct mechanical contact with the object to be inspected. A suitable non-contact generator may be an air-coupled transducer that includes a mechanical vibrating transducer (e.g., such as a piezoelectric element or a capacitive element) that can controllably oscillate to produce the ultrasonic waves applied to the object. The output port of such a generator is placed proximate to the object, and emitted ultrasonic waves are directed to the object at the application point via an air layer separating the output port of the generator and the object. Another suitable non-contact ultrasonic generator may include a generator with an electromagnetic-acoustic transducer (EMAT). In an EM acoustic transducer, a current may be induced to flow in the surface by using a coil positioned proximate to the surface of the object, and a solenoid/permanent magnet causes a magnetic field to be generated perpendicular to the current flow, to thus cause a force to be exerted on the object. The stress fields resulting from the exerted force cause ultrasonic waves to be generated. Yet another suitable non-contact generator is a pulsed laser ultrasonic generator that applies laser radiation to the object at the application point to cause waves to be generated in the object in either the thermoelastic regime or the ablative regime. In another non-contact inspection technique, referred to as Eddy Current testing, a coil generates a changing magnetic field which generates eddy currents. Variations in the phase and magnitude of these eddy currents can be monitored using the same or a different coil, and/or by measuring changes to the current flowing in the first (excitation) coil.

Other types and/or implementations of generators to cause waves to travel in the object to be inspected may also be used.

Figure 2B:
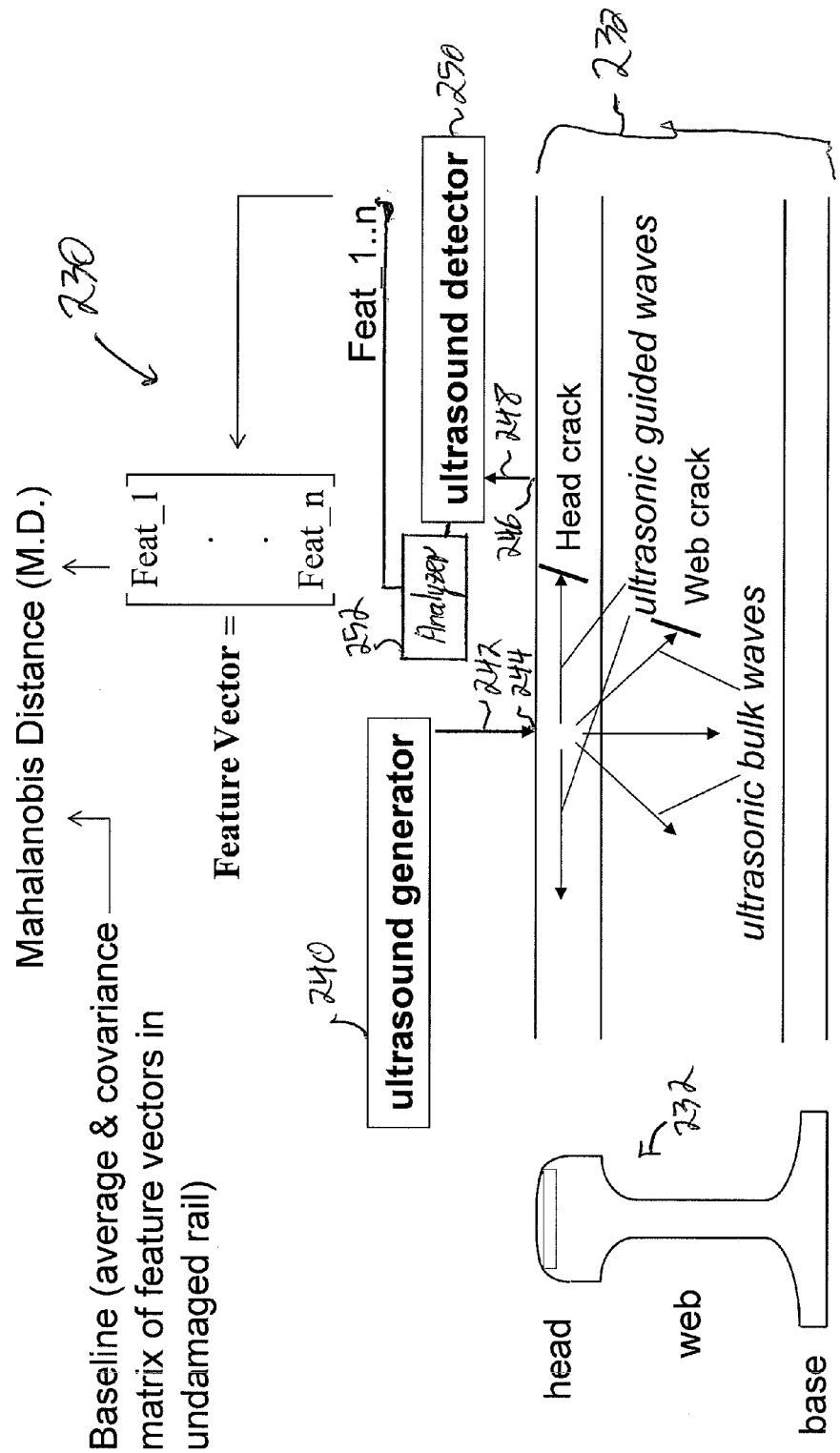
FIG. 2B is a schematic diagram of an example of an inspection system in a pitch-catch configuration (e.g., one generator and one detector)
Figure 2C:
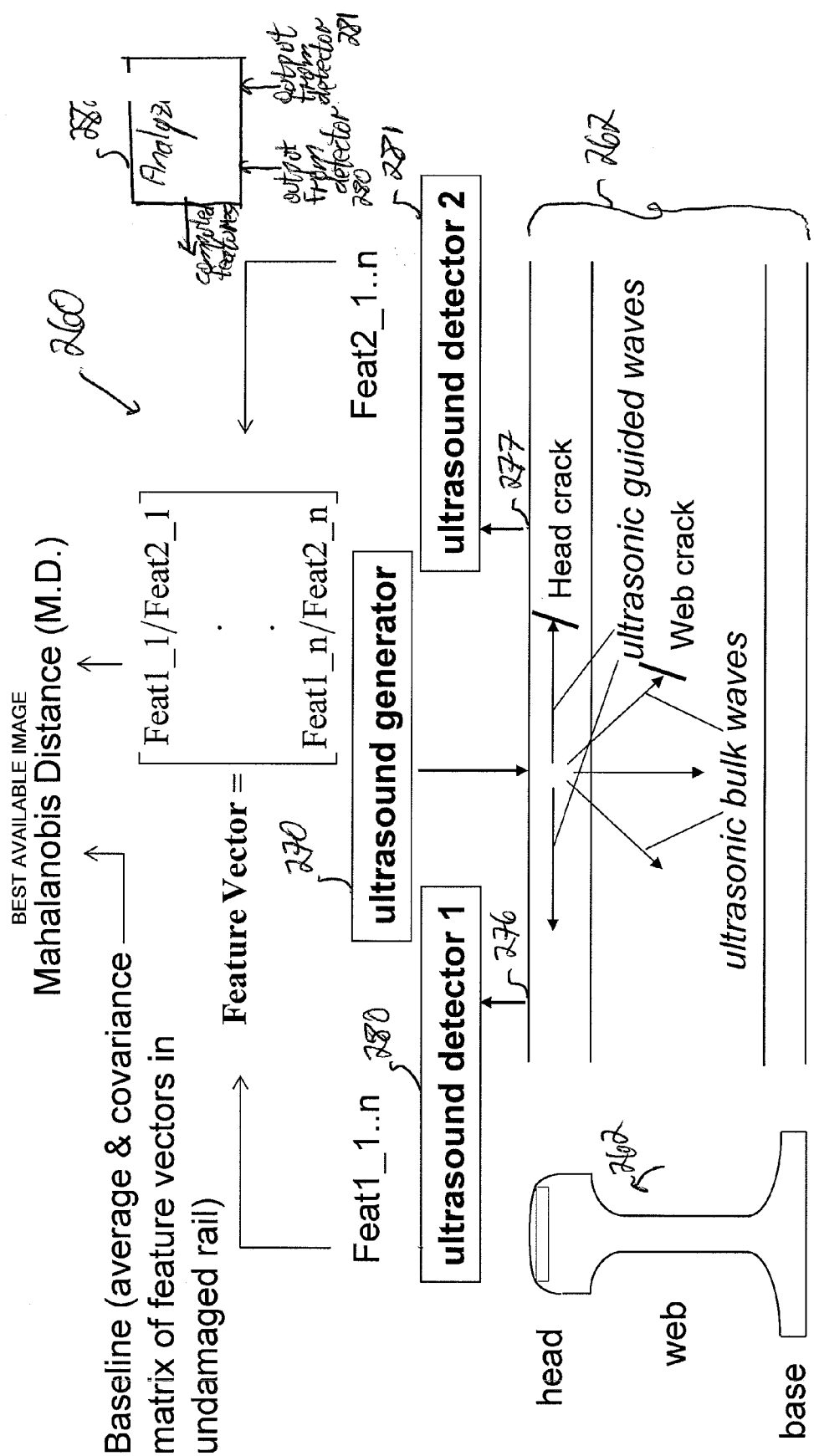
FIG. 2C is a schematic diagram of an example of an inspection system in a pitch-catch configuration with multiple detectors.

Thus, a generator excites waves (e.g., ultrasonic waves) in the object (in the system depicted in FIG. 2A, at the top of the railhead). The excited waves (e.g., ultrasonic) travel in the object 202. The traveling waves include, for example, bulk waves (longitudinal or shear waves) that may be reflected at edges of the object or when encountering a defect, as well as other waves traveling in different directions (e.g. guided waves, e.g. Rayleigh waves, traveling substantially parallel to the longitudinal axis of the object). At least a portion of the waves traveling in the object 202 is detected by a detector 220 (the detected portion is indicated by the arrow marked 218). In the embodiments of FIG. 2A, the detector 220 is included in the generator 210. For example, a contact-based generator implemented using a piezoelectric transducer may use the same transducer to detect returning traveling waves. Returning ultrasonic sound waves cause vibration of the piezoelectric transducer, which in turn cause the transducer to generate a voltage that is a function of the properties (e.g., amplitude, frequency) of the detected portion of the waves. In some implementations, the contact-based generator may include a separate transducer to cause ultrasonic waves in the object, and another transducer to detect at least a portion of the waves (see, for example, FIG. 2B, showing a pitch-catch configuration). In some implementations of the pitch-catch configuration, the generator may be used with multiple detectors (FIG. 2C). In some embodiments, a non-contact generator may also include a detector to detect at least a portion of the waves traveling in the object. For example, in a laser acoustic generator, a reflected beam of a laser device (same as the one that caused the ultrasonic waves, or a different laser device) may be examined by an interferometer. Small shifts in the frequency of the reflected laser beam or shifts in the length of the optical beam path caused by ultrasonic waves causing vibrations at the surface of the object can be identified by the interferometer. In some embodiments, the detector may include a microphone to detect ultrasonic waves. Although one detector is referred to in relation to FIG. 2A (namely, the detector 220), several detectors may be used with the system/apparatus of FIG. 2A. In some embodiments, the generator/detector can be an electromagnetic-acoustic transducer (EMAT) device.

In some implementations, the detector may be configured to detect particular types of waves by controlling, for example, a time window during which the detector detects traveling waves. For example, certain waves may be reflected from one surface and reach the surface near which the detector is located during some estimated time period, while other types of waves may reach the detector at other estimated time periods. Thus, by detecting traveling waves at pre-determined time periods, the detector may be configured to detect particular waves (bulk waves or guided waves) that traveled over some estimated path. As will be described in greater detail below, the behavior of the at least portion of the waves detected (represented, for example, by feature values derived from the detected waves) is compared to features of baseline waves recorded in an undamaged (i.e., defect-free) portion of the object and therefore representing the "normal" condition of the object. Accordingly, controlling and/or determining which waves were detected (by controlling, for example, the time window) can enable proper comparison of the detected waves to a proper "baseline" wave.

In some embodiments, the generator 210 may cause waves having at least two different frequencies to travel through the object to enhance defect detection sensitivity at different object depths. Generally, at least some ultrasonic waves of a particular frequency band in an object will be more sensitive to defects at a particular object depth, while ultrasonic waves of a different frequency band may be sensitive to defects at another depth. For example, the frequencies of the ultrasonic guided waves are inversely proportional to the wave penetration depth in an object and thus higher frequency guided waves may be more sensitive to defects closer to the surface (where the energy was applied), whereas "low-frequency" guided waves may be more sensitive to defects farther away from the surface where the generator was applied.

The detector 220 produces output responsive to the detected portion of the waves. For example, the detector 220 may produce data that is representative of the behavior (e.g., the amplitude as a function of time) of the detected portion of the waves. The output produced is provided to a statistical analyzer 222 configured to perform a statistical analysis based on a current output produced by the detector and the distribution of similar outputs previously collected in an undamaged portion of the rail which represent the rail's "normal" or "baseline" behavior, in response to the detected portion of the waves. The statistical analysis performed by the analyzer 222 may then be used to determine whether at least one defect is present in the object. In some embodiments, the analyzer may be part of the generator 210 and/or the detector 220 (i.e., it may constitute a module of an integrated system that may include the generator, detector and/or the analyzer), or the analyzer 222 may be a physically separate unit from the generator 210 and/or the at least one detector 220.

Generally, the analyzer 222 compares behavior of the detected portion of the waves to a baseline behavior of waves in an undamaged (e.g., defect-free) object. The baseline behavior can be determined at an earlier point of time by causing waves (ultrasonic waves) to be excited in an object that is similar to the object that is being inspected, and is known not to be damaged. Additionally, in determining such a behavior baseline, a detector similar to the detector 220 used to inspect the current object is used to detect waves at approximately the same position and using approximately the same time window so that the baseline waves will have a behavior that would be similar to the behavior of the current waves detected by the detector 220 if the section/area of the object being inspected were also defect-free. If, on the other hand, the behavior of portion of the waves detected by the detector 220 is statistically much different than the previously determined baseline behavior, this would be indicative that there is a significant likelihood that the section of the object being inspected may have a defect (e.g., a crack).

In some embodiments, the statistical analysis is performed by computing (or deriving) values for particular features that may be representative of the behavior of the detected portion of the waves. As noted, in some embodiments, the detector 220 may produce output representative of the amplitude of the detected portion of the waves as a function of time. In such embodiments, the representative statistical values that can be computed from the output produced (and subsequently compared to a baseline of features corresponding to waves traveling in an undamaged object) may include one or more of the following values: a) root-mean square of the amplitude of the detected portion of the waves, b) variance of the amplitude of the detected portion of the waves, c) cross-correlation value of the amplitude of the detected portion of the waves, d) auto-correlation value of the amplitude of the detected portion of the waves, e) peak-to-peak value of the amplitude of the detected portion of the waves, f) peak value of the amplitude of the detected portion of the waves, g) Kurtosis value (e.g., a measure of the peakedness of the source signal, where a higher Kurtosis value implies more of the variance due to infrequent extreme deviations) of the amplitude of the detected portion of the waves, h) at least one other time-domain Statistical Moment corresponding to properties of the detected portion of the waves, i) at least one other frequency-domain Statistical Moment corresponding to the properties of the detected portion of the waves, and j) normalized values of any of feature values.

The feature values computed are arranged into a feature vector, such as the feature vector 226 depicted in FIG. 2A. The feature vector 226 may include n feature values (denoted by "Feat_1, . . . , Feat_n), where n≥1 (i.e., the feature vector includes one or more computed feature values). That is:

$$\text{Feature Vector} = \begin{bmatrix} \text{Feat\_1} \\ \vdots \\ \text{Feat\_n} \end{bmatrix}$$

Generally, increasing the number of features improves the sensitivity of the statistical analysis to the presence of the defects.

A baseline statistics measured in a defect-free portion of the rail and representing the rail "normal" behavior is subsequently compared to the just computed feature vector to determine how closely the feature vector statistically matches the baseline distribution. To statistically compare the current feature vector to the baseline statistical distribution, various outlier-analysis procedures, discordancy tests or anomaly detection procedures are performed by, for example, the analyzer 222 to identify significant variations between the current feature vector and the normal rail behavior.

In some implementations, the outlier-analysis or discordancy test procedure used may be a Mahalanobis Squared Distance (or "M.S.D."), which is a type of a multivariate outlier analysis procedure. Specifically, M.S.D. determines the similarity of an unknown sample set (in this case, the feature vector derived from the currently detected portion of the waves) to a known one (in this case the baseline distribution). M.S.D. generally takes into account the correlations of the data set and is scale-invariant. The M.S.D. is defined as:

$$\text{Mahalanobis Squared Distance (M.S.D.)} = (x - \bar{x})^T \times Cov^{-1} \times (x - \bar{x})$$

where x is the current feature vector for the detected portion of the wave, $\bar{x}$ is the mean of the baseline feature vectors, $C_{ov}$ is the covariance matrix of the baseline feature vectors, $^T$ represents a transpose operation and $^{-1}$ represents an inverse matrix operation.

In some embodiments, other procedures/analyses that may be used to perform outlier analysis, discordancy test or anomaly detection include, for example, Principal Component Analysis, Factor Analysis, Cluster Analysis, Linear Discriminant Analysis, Mean-Square-Error analysis/computations, Euclidean Distance analysis, etc.

Having computed the statistical analysis metric, the computed value may be used to determine if a defect may be present in the object. In some implementations, a currently computed analysis metric (or data point), for example, the computed M.S.D. metric, is compared to a pre-determined threshold. The metric may be determined to be indicative of a defect at the inspected area of the object if the metric value exceeds a pre-determined threshold. The pre-determined threshold is generally selected to exceed a certain level of statistical confidence that a current feature vector is outside the baseline distribution.

As noted, in situations where the object is inspected at multiple locations, for example, when the object is of a length that requires movement of the inspection system, the statistical analysis is performed for multiple locations, and the resultant computed metric (e.g., M.S.D. metric) may be recorded as a function of the moving application point. For example, when the object being inspected is a rail, the statistical analyzer 222 records the metrics computed by the particular outlier procedure used as a function of the location of the moving application point 214. The recorded metrics may be plotted in real-time (or otherwise) as the inspection moves along the rail as a function of the location of the moving application point 214 to thus provide a graph that can visually indicate potential locations in the object where a defect may be present (see the graphs 530 and 540 of FIG. 5 for examples of such graphs).

With reference to FIG. 2B, a schematic diagram of an example inspection system 230 is shown. The system 230 is generally similar to the system 200 of FIG. 2A, except that in embodiments of the system 230 a detector 250 to detect at least a portion of the waves traveling in an object 232 (the object 232 in FIG. 2B is also a rail) is a separate device from a generator 240 that is used to cause waves (e.g., ultrasonic waves) to be excited in the object and travel therein. Thus, in operation, the generator 240, which may similar to the generator 210 described in relation to FIG. 2A and may be a contact or non-contact generator, applies energy (marked with arrow 242) at an application point 244 of the object 232. The applied energy causes, for example, ultrasonic waves to travel in the object. At least a portion of the waves (indicated by arrow 248) is detected by the detector 250 at a detection position 246. The detector 250 may be similar to the detector 220 described in relation to FIG. 2A. As with the detector 220, the detector 250 may also be configured to selectively detect particular types of waves by using, for example, a time window. Thus, in some embodiments, the detector 250 can detect different portions of the waves (e.g., bulk waves, guided waves, etc.) by adjusting the time window during which the detector detects the waves traveling in the object 232.

The detector 250 produces output responsive to the detected portion of the waves. The output produced is representative of the behavior of the detected at least the portion of the waves. A statistical analyzer 252, which may be similar to the statistical analyzer 222 of FIG. 2A, performs a statistical analysis using the output to determine if a defect is present in the object. The analysis may also provide additional information about the location and nature of the defect. In some embodiments, the analyzer 252 performs an outlier analysis, discordancy test or anomaly detection (e.g., such as the M.S.D. procedure described herein) by comparing derived features representative of the behavior of the detected portions of the waves to a baseline of feature values representative of the "normal" behavior of the rail. The comparison can thus provide information on whether the behavior of the detection portion of the waves is anomalous relative to the baseline ("normal") behavior.

With reference to FIG. 2C, a schematic diagram of an example inspection system 260 is shown. The system 260 includes two detectors 280 and 281 that are each configured to detect a different portion of the waves at respective location 276 and 277. Each of the detectors 280 and 281 may be similar to any of the detectors 220 and 250 shown in FIGS. 2A and 2B, respectively. The system 260 further includes at least one generator 270 to cause waves (such as ultrasonic waves) to travel in the object 262 (here too, the depicted object 262 is a rail). The generator 270 may be similar to any of the generator 210 and/or 240 shown in FIGS. 2A and 2B, respectively.

In some embodiments, the behavior of the waves traveling in the object can be represented by computing the ratios of the feature values (which may be similar to the features described in relation to the system 200 of FIG. 2A) computed for the respective portions of the waves detected in the two detectors 280 and 281, thus enabling determination of the existence of defects based on data collected at the two detectors. Other ways to compute representative values that are based on the output produced at the two detectors in response to detecting the respective portions of the waves may be used. In system configurations that include more than two detectors, similar techniques to compute consolidated representative feature values (e.g., compute the ratios of features values computed from the outputs produced by the multiple detectors) may be used.

Thus, a statistical analyzer 282 receives the outputs of the two detectors 280 and 281 and computes the respective feature values from each of those outputs. In some embodiments, a single analyzer at one of the detectors or at some remote location receives and processes the outputs. In some embodiments, each detector may be coupled to a dedicated analyzer and the various computations may be performed in a distributed manner. As noted above, such feature values may include, but are not limited to, one or more of the following: a) root-mean square of the amplitude of detected portions of the waves, b) variance of the amplitude of the detected portions of the waves, c) cross-correlation value of the amplitude of the detected portions of the waves, d) peak-to-peak value of the amplitude of the detected portions of the waves, e) peak value of the amplitude of the detected portions of the waves, f) Kurtosis value of the amplitude of the detected portions of the waves, g) at least one other time-domain Statistical Moment corresponding to properties of the detected portions of the waves, h) at least one other frequency-domain Statistical Moment corresponding to the properties of the detected portions of the waves, and i) normalized values of any of the aforementioned feature values. Having computed the respective feature values, the respective ratios between each of the features computed by the two detectors are then calculated (e.g., as ratio features). The ratio features are arranged (assembled) in a feature vector, x, which, as was done in relation to the system 200 of FIG. 2A, may be updated at each inspection position of the object (in situations where energy from the generator 270 is applied at a moving application point). Feature vector, x, may thus be represented as:

$$\text{Feature Vector} = \begin{bmatrix} \text{Feat1\_1}/\text{Feat2\_1} \\ \vdots \\ \text{Feat1\_n}/\text{Feat2\_n} \end{bmatrix}$$

As noted, in situations involving a single detector (FIGS. 2A and 2B), the feature vector is calculated using features from the single detector, i.e.:

$$\text{Feature Vector} = \begin{bmatrix} \text{Feat\_1} \\ \vdots \\ \text{Feat\_n} \end{bmatrix}$$

The feature vector x is subsequently statistically compared to the "baseline distribution" that includes a set of measurements acquired for an undamaged object similar to the object 262 using a system configuration similar to the configuration of the system 260 of FIG. 2C. Thus, in acquiring the baseline distribution, feature values for respective portions of waves detected by one or multiple detectors configured similarly to the detectors in FIG. 2A, 2B or 2C. The waves traveling in the object used to compute the baseline distribution are generated in a manner similar to the generation of waves in the object 202 and/or 232. The "baseline distribution" needs only to be taken once for a particular type of object (e.g., for a particular type of rail).

The statistical comparison may be performed, in some embodiments, based on an outlier analysis, discordancy test or anomaly detection procedure such as the "Mahalanobis Squared Distance" (M.S.D.) described above. Thus, the M.S.D. metric may be computed based on the equation:

$$\text{Mahalanobis Squared Distance (M.S.D.)} = (x-\bar{x})^T \times Cov^{-1} \times (x-\bar{x})$$

where x is the feature ratio vector populated by the features computed from the output of the detectors, $\bar{x}$ is the mean ratio vector of the baseline, $C_{ov}$ is the covariance matrix of the baseline, $^T$ represents the transpose operation and $^{-1}$ represents the inverse matrix operation. A current M.S.D. data point, computed based on ratios of feature values derived from outputs produced by the detector is classified as a defect if its value exceeds a pre-determined threshold.

As noted above, if the signal features are computed from the ultrasonic measurements at different frequency bands, several M.S.D. metrics can be computed for the different ultrasonic frequencies. Because the frequency of an ultrasonic guided wave is inversely proportional to the wave penetration depth into the railhead, where the detectors are configured to detect guided waves (e.g., by controlling the detectors' positioned, the time windows during which they are active, etc.) in a rail having a structure similar to that of the rail 262, the "high-frequency" M.S.D. will be more sensitive to surface head defects, whereas the "low-frequency" M.S.D. will be more sensitive to internal defects. Hence, in such implementations it is possible to classify the defects rather than simply detecting them. In some embodiments, a M.S.D.

computed for 700 kHz waves enables detecting cracks as deep as about 5 mm (millimeter) into the rail head, whereas a M.S.D. computed for 200 kHz waves enables detecting at deeper depth in the rail head. Generally, in some embodiments, frequency bands in the range of 20 KHz to 5 MHz may be used. Alternatively, other frequency ranges may be used.

Any of the analyzers 222, 252 and 282 may be implemented as a processor-based systems that include a computer and/or other types of processor-based devices suitable for multiple applications. Such devices can include volatile and non-volatile memory elements, and peripheral devices to enable input/output functionality.

Figure 3:
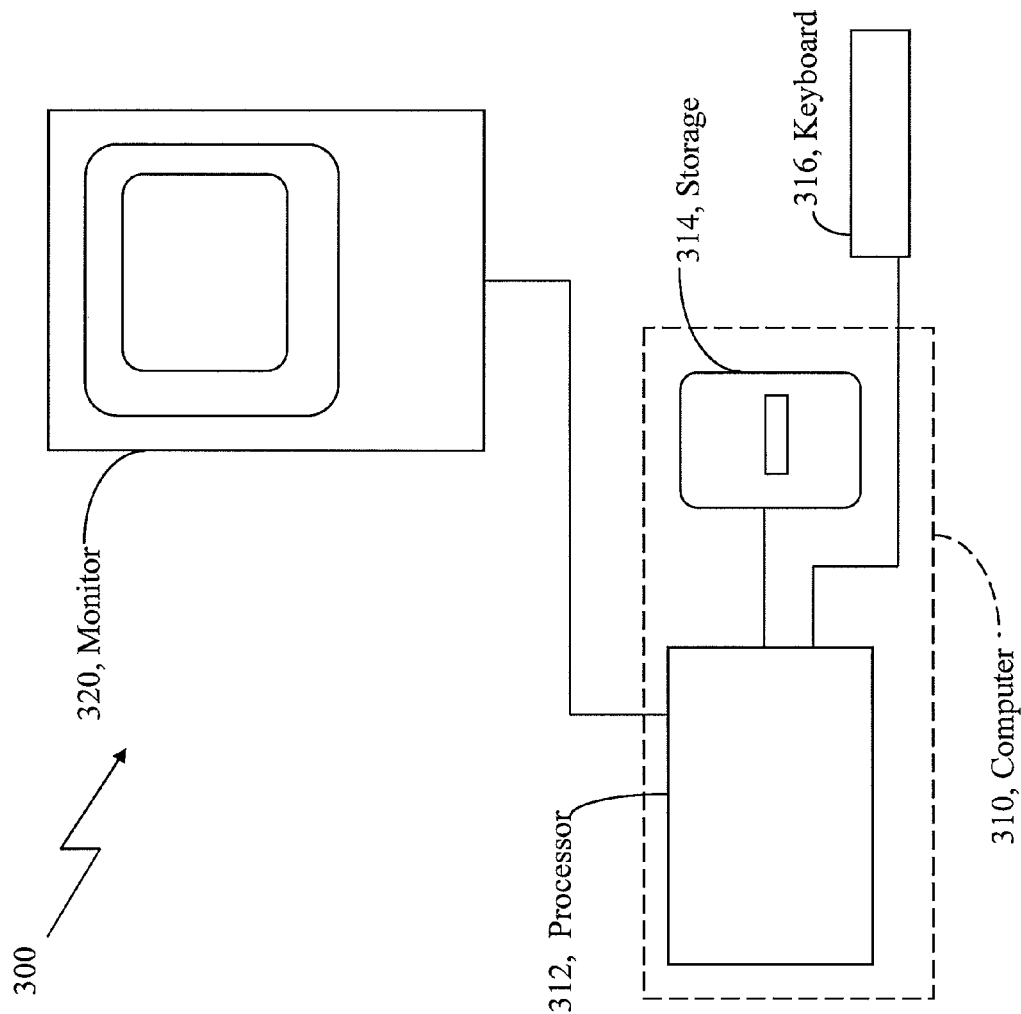
FIG. 3 is a schematic diagram of a generic computing system that may be used to implement, for example, the statistical analyzer shown in FIGS. 2A-2C.

Specifically, and with reference to FIG. 3 showing a schematic diagram of a generic computing system 300 that may be used to implement the processor-based analyzer, the computing system 300 includes a processor-based device 310 such as a personal computer, a specialized computing device, and so forth, that typically includes a central processor unit 312. In addition to the CPU 312, the system includes main memory, cache memory and bus interface circuits (not shown). The processor-based device 310 includes a mass storage element 314, such as a hard drive associated with the computer system. The computing system 300 may further include a keyboard, or keypad, 316, and a monitor 320, e.g., a CRT (cathode ray tube) or LCD (liquid crystal display) monitor.

The processor-based device 310 is configured to facilitate, for example, the implementation of the object-inspection, including implementation of the statistical outlier analysis procedure. The storage device 314 may thus include a computer program product that when executed on the processor-based device 310 causes the processor-based device to perform operations to facilitate the implementation of object inspection to determine if there are defects present in the object. The processor-based device may further include peripheral devices to enable input/output functionality. Such peripheral devices may include, for example, a CD-ROM drive and/or floppy drive, or a network connection, for downloading related content to the connected system. Such peripheral devices may also be used for downloading software containing computer instructions to enable general operation of the respective system/device. Alternatively and/or additionally, in some embodiments, special purpose logic circuitry, e.g., an FPGA (field programmable gate array) or an ASIC (application-specific integrated circuit) may be used in the implementation of the system 300. Other modules that may be included with the processor-based device 310 are speakers, a sound card, a pointing device, e.g., a mouse or a trackball, by which the user can provide input to the computing system 300. The processor-based device 310 may include an operating system, e.g., Windows XP® Microsoft Corporation operating system. Alternatively, other operating systems could be used.

The computing system 300 may be connected using conventional network arrangements (e.g., to connect several analyzers in implementations where more than one analyzer is used). Other types of network communication protocols may also be used to communicate between the various systems and systems/devices. Alternatively, the systems and devices may each be connected to network gateways that enable communication via a public network such as the Internet. Network communication may be used to link any of the statistical analyzers 222, 252 and/or 282 to a remote computing system using wireless or wire-based links. The computing system 300 may include a communication device (e.g., an antenna, a transceiver such as a network gateway portal connected to a network, etc.) to transmit and receive data signals. Further, dedicated physical communication links, such as communication trunks may be used. Some of the various systems described herein may be housed on a single processor-based device (e.g., a server) configured to simultaneously execute several applications.

Figure 4:
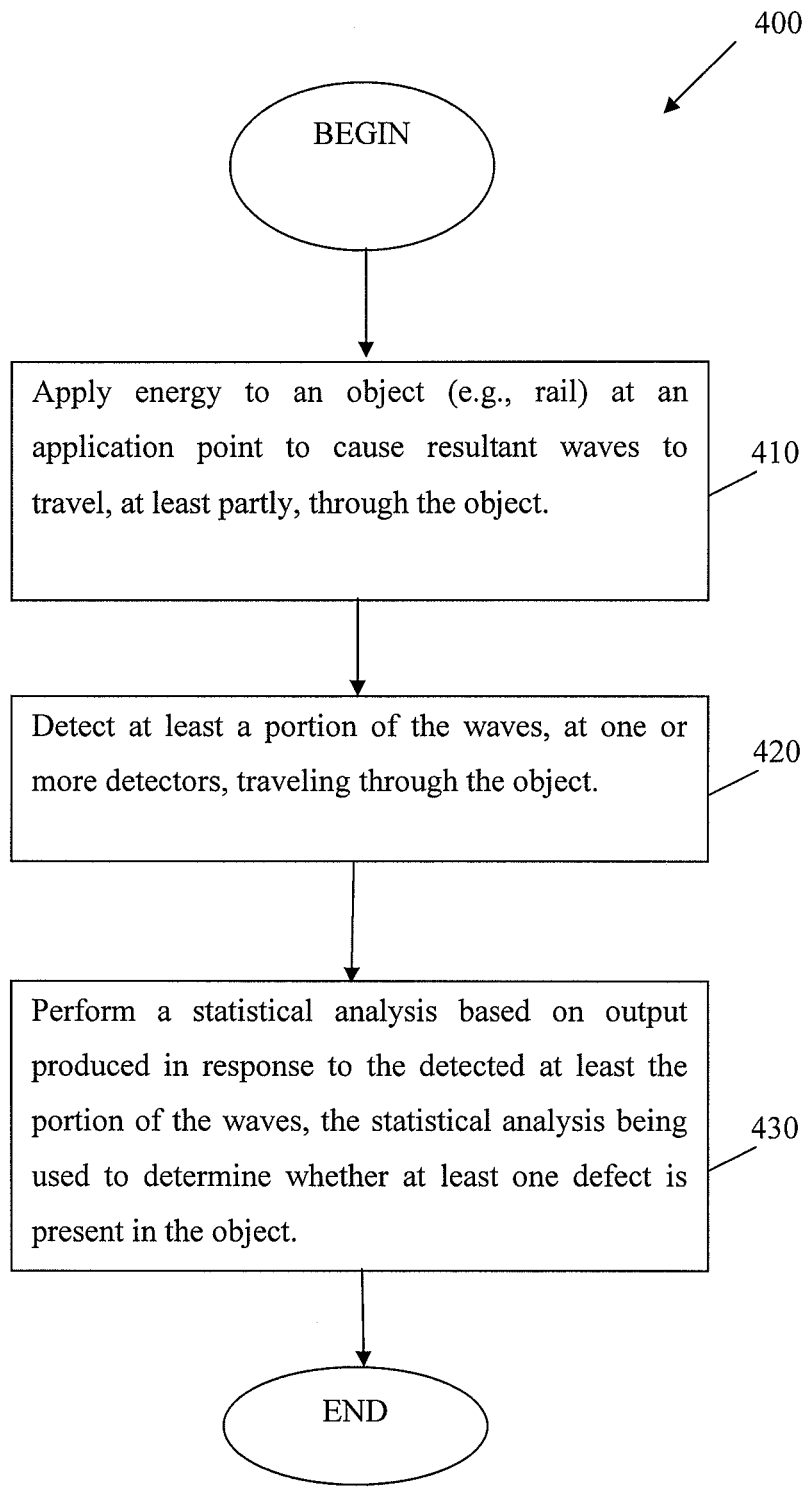
FIG. 4 is a flowchart of a statistical-based analysis inspection procedure.

With reference to FIG. 4, a flowchart of an inspection procedure 400 that is based on a statistical-based analysis of acquired data is shown. To perform the inspection procedure, energy is applied 410 to an object at an application point to cause resultant waves (e.g., ultrasonic waves) to travel, at least partly, through the object. The energy may be applied by one or more generators which may include contact type generators (e.g., piezoelectric transducers, ultrasonic wheels, ultrasonic sleds, water coupled generators, etc.), or by a non-contact generator (such as a laser acoustic system, air-coupled transducers, electromagnetic-acoustic transducer (EMAT), eddy current transducer, etc.)

Having caused waves to travel in the object (an object such as a rail), at least a portion of the waves traveling through the object is detected 420 by one or more detectors. The detectors are configured to detect, for example, acoustic waves, including ultrasonic waves, and can be controllably configured to detect particular types of waves, e.g., guided waves, bulk waves (i.e. longitudinal waves and/or shear waves), etc., by, for example, controlling the time window during which the detectors detect waves, as well as the wave generation angles. A detector may be the same device as the generator (e.g., an acoustic transducer implemented using, for example, a piezoelectric element, may operate as both a generator and a detector, e.g., pulse-echo configuration), may otherwise be included with the same device as the generator, or may be a device separate from the generator and positioned in a different location, e.g., pitch-catch configuration.

Having detected at least a portion of waves, a statistical analysis based on output produced in response to the detected at least the portion of the waves is performed 430. The statistical analysis may then be used to compare the current response to the statistical distribution of "normal" (defect-free) responses of the rail, to determine whether at least one defect is present in the rail. The statistical analysis may be, in some implementations, an outlier analysis, a discordancy test or an anomaly detection procedure such as the Mahalanobis Squared Distance technique to determine outlying behavior that may be indicative of anomalous behavior by the detected signals (and thus indicative that the outlying behavior may have occurred because of a defect). Other unsupervised statistical-based techniques may be applied to the output produced by the one or more detectors, including other outlier techniques, such as Principal Component Analysis, Factor Analysis, Cluster Analysis, Linear Discriminant Analysis, Mean-Square-Error analysis/computations, Euclidean Distance analysis, etc.

Figure 5:
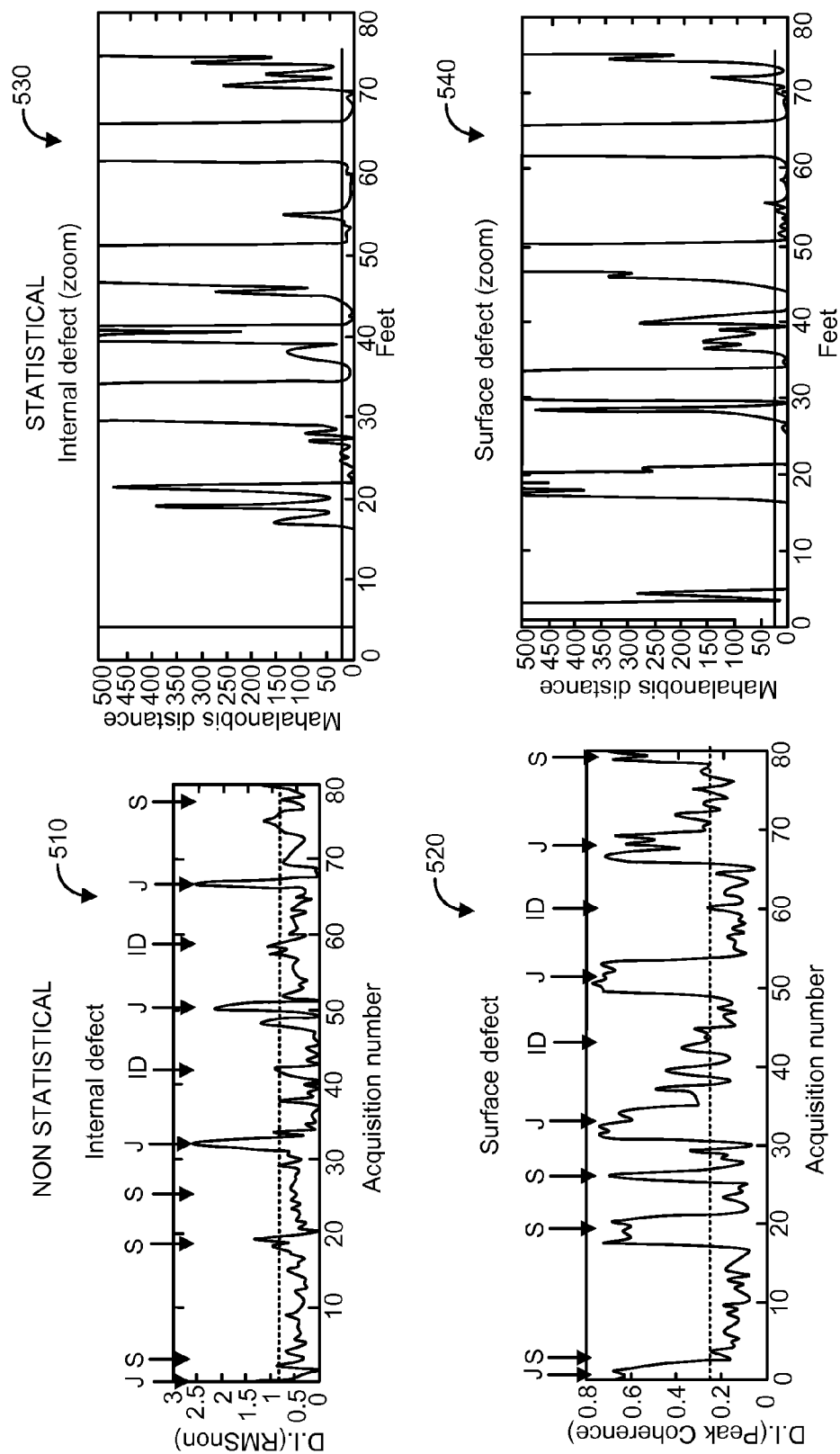
FIG. 5 includes example plots generated using non-statistical and statistical analysis procedures of data acquired by inspection systems.

FIG. 5 compares results from non-statistical analyses (plots 510 and 520) to results obtained by an M.S.D. statistical-based analysis (plots 530 and 540) computed, for example, using one of the systems shown in FIGS. 2A-C. The statistical analysis described herein was performed in relation to a section of rail with known defects. The horizontal lines in the plots represent the thresholds beyond which a data point may be flagged as a defect. Also marked on graphs 510 and 520 are locations of various structural anomalies in the object that was being inspected using a conventional non-statistical procedure. Those structural anomalies include internal cracks (identified with the label "ID") and surface cracks (identified with the label "S"). The graphs 510 and 530 correspond to analyses performed using a first frequency band better suited to detect internal defects, while the graphs 520 and 540 correspond to analyses performed using a second frequency band better suited to detect surface cracks. As shown, the graphs 530 and 540 illustrate the computation results obtained using a statistical-based analyses (in this case, M.S.D.-based analysis) provided a substantial improvement in defect detection reliability compared to the results obtained using non-statistical analyses (e.g., the graphs corresponding to the statistical-based analyses include higher peaks corresponding to the defects).

The systems and methods disclosed herein may be embodied in various forms including, for example, a data processor, such as a computer that also includes a database, digital electronic circuitry, firmware, software, or in combinations of them. Moreover, the above-noted features and other aspects and principles of the present disclosed embodiments may be implemented in various environments. Such environments and related applications may be specially constructed for performing the various processes and operations according to the disclosed embodiments or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the disclosed embodiments, or it may be more convenient to construct a specialized apparatus or system to perform the required methods and techniques.

The systems and methods disclosed herein may be implemented as a computer program product, i.e., a computer program tangibly embodied in an information carrier, e.g., in a machine readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

The foregoing description is intended to illustrate but not to limit the scope of the invention, which is defined by the scope of the appended claims. Other embodiments are within the scope of the following claims.

What is claimed is:

1. A system comprising:
    at least one generator configured to apply energy to an object at an application point to cause waves to travel, at least partly, through the object;
    at least one detector configured to detect at least a portion of the waves traveling through the object; and
    a statistical analyzer configured to perform a statistical analysis based on an output produced by the at least one detector in response to the detected portion of the waves, the statistical analysis being used to determine whether at least one defect is present in the object, wherein the statistical analysis performs on the output of the at least one detector one or more of an outlier analysis, a discordancy test, and an anomaly detection, by at least computing one or more variation values between feature values of the detected portion of the waves and corresponding baseline feature values computed for a defect-free section of a representative object having a profile substantially similar to the profile of the object, and
    wherein the feature values include one or more of a root-mean square of an amplitude of the detected portion of the waves, a variance of the amplitude of the detected portion of the waves, a cross-correlation value of the amplitude of the detected portion of the waves, an auto-correlation value of the amplitude of the detected portion of the waves, a peak-to-peak value of the amplitude of the detected portion of the waves, a peak value of the amplitude of the detected portion of the waves, a Kurtosis value of the amplitude of the detected portion of the waves, a time-domain statistical moment corresponding to properties of the detected portion of the waves, a frequency-domain statistical moment corresponding to the properties of the detected portion of the waves, and one or more normalized values of one or more of the feature values.

2. The system of claim 1, wherein the statistical analyzer configured to compute the one or more variation values between feature values of the detected portion of the waves and the corresponding baseline feature values is configured to at least: compute a value based on the equation:

$$\text{Mahalanobis Squared Distance (M.S.D.)} = (x-\bar{x})^T \times Cov^{-1} \times (x-\bar{x})$$

where x is a vector of the computed feature values, is the mean vector of the corresponding baseline feature values, represents a covariance matrix operation, T represents a transpose operation and −1 represents an inverse matrix operation.

3. The system of claim 1, wherein the object includes a rail of a railroad track, and wherein the at least one defect includes an internal crack in the rail.

4. The system of claim 1, wherein the at least one generator includes the at least one detector.

5. The system of claim 1, wherein the at least one generator is configured to at least apply energy to the object at a moving application point.

6. The system of claim 1, wherein the at least one generator to apply energy to the object is configured to at least:
    apply energy to cause acoustic bulk waves, including one or more of longitudinal waves and shear waves, to travel through the object at specified angles to enhance the defect detection sensitivity.

7. The system of claim 1, wherein the at least one detector is configured to at least detect the portion of the waves within a pre-determined time window.

8. The system of claim 7, wherein the statistical is configured to at least:
    determine one or more variation values between features of respective portions of bulk waves detected by the at least one detector.

9. The system of claim 1, further including at least one device configured to act as the generator and the detector.

10. The system of claim 1, wherein the at least one generator is configured to at least:
    apply energy to cause acoustic waves having one or more components with corresponding frequencies to travel through the object to enhance the defect detection sensitivity at one or more object depths.

11. The system of claim 1, wherein the at least one generator includes one or more of: an ultrasonic wheel generator, an ultrasonic sled generator, a water-coupled generator, a laser acoustic device, air-coupled transducer, an electro-magnetic acoustic transducer (EMAT) and a mechanical impactor.

12. The system of claim 1, wherein the at least one generator is contained in a first wheel and the at least one detector is contained in a second wheel.

13. The system of claim 1, wherein the at least one generator comprises a first piezoelectric transducer contained in a first wheel configured to roll on a rail and to induce in the rail at least one of a plurality of first ultrasonic guided waves, and the at least one detector comprises a second piezoelectric transducer contained in a second wheel configured to roll on the rail and to detect at least one of a plurality of second ultrasonic guided waves propagating in the rail.

14. The system of claim 13, wherein the first wheel and the second wheel each include an inner cylindrical cavity containing a fluid.

15. The system of claim 13, wherein the at least one of the plurality of first ultrasonic guided waves travels in a direction substantially parallel to a longitudinal axis of the rail.

16. The system of claim 13, wherein the at least one of the plurality of second ultrasonic guided waves travels in a direction substantially parallel to a longitudinal axis of the rail.

17. The system of claim 12, wherein the first wheel and the second wheel are the same wheel.

18. The system of claim 12, wherein the first wheel and the second wheel are separate wheels.

19. A method comprising:
applying energy to an object at an application point to cause resultant waves to travel, at least partly, through the object;
detecting at least a portion of the waves traveling through the object; and
performing, by a statistical analyzer, a statistical analysis based on output produced in response to the detected portion of the waves, the statistical analysis being used to determine whether at least one defect is present in the object, wherein the statistical analysis performs on the output of the at least one detector one or more of an outlier analysis, a discordancy test, and an anomaly detection, by at least computing one or more variation values between feature values of the detected portion of the waves and corresponding baseline feature values computed for a defect-free section of a representative object having a profile substantially similar to the profile of the object, and
wherein the feature values include one or more of a root-mean square of an amplitude of the detected portion of the waves, a variance of the amplitude of the detected portion of the waves, a cross-correlation value of the amplitude of the detected portion of the waves, an auto-correlation value of the amplitude of the detected portion of the waves, a peak-to-peak value of the amplitude of the detected portion of the waves, a peak value of the amplitude of the detected portion of the waves, a Kurtosis value of the amplitude of the detected portion of the waves, a time-domain statistical moment corresponding to properties of the detected portion of the waves, a frequency-domain statistical moment corresponding to the properties of the detected portion of the waves, and one or more normalized values of one or more of the feature values.

20. The method of claim 19, wherein computing one or more variation values comprises:
computing a value based on the equation:

$$\text{Mahalanobis Squared Distance (M.S.D.)} = (x-\bar{x})^T \times Cov^{-1} \times (x-\bar{x})$$

where x is a vector of the computed feature values, is the mean vector of the corresponding baseline feature values, represents a covariance matrix operation, T represents a transpose operation and −1 represents an inverse matrix operation.

21. The method of claim 19, wherein applying energy to the object comprises: applying energy to cause acoustic waves having one or more components with corresponding frequencies to travel through the object to enhance the defect detection sensitivity at one or more object depths.

22. The method of claim 19, wherein detecting the portion of the waves comprises:
detecting portions of the waves by two or more detectors positioned at one of: different sides of the application point and on the same side of the application point.

23. The method of claim 19, wherein the feature values include one or more of:
a root-mean square of an amplitude of the detected portion of the waves, a variance of the amplitude of the detected portion of the waves, a cross-correlation value of the amplitude of the detected portion of the waves, an auto-correlation value of the amplitude of the detected portion of the waves, a peak-to-peak value of the amplitude of the detected portion of the waves, a peak value of the amplitude of the detected portion of the waves, a Kurtosis value of the amplitude of the detected portion of the waves, a time-domain statistical moment corresponding to properties of the detected portion of the waves, a frequency-domain statistical moment corresponding to the properties of the detected portion of the waves, and one or more normalized values of one or more of the feature values.

24. The method of claim 19, wherein applying energy to the object comprises:
applying energy to cause acoustic bulk waves, including one or more of longitudinal waves and shear waves, to travel through the object at specified angles to enhance the defect detection sensitivity.

25. A non-transitory computer program product residing on a computer readable medium and comprising computer instructions that when executed on a processor-based device cause the processor-based device to at least:
perform a statistical analysis based on output produced in response to detected at least a portion of waves traveling through an object, the statistical analysis being used to determine whether at least one defect is present in the object, a statistical analyzer configured to perform a statistical analysis based on an output produced by the at least one detector in response to the detected portion of the waves, the statistical analysis being used to determine whether at least one defect is present in the object, wherein the statistical analysis performs on the output of the at least one detector one or more of an outlier analysis, a discordancy test, and an anomaly detection, by at least computing one or more variation values between feature values of the detected portion of the waves and corresponding baseline feature values computed for a defect-free section of a representative object having a profile substantially similar to the profile of the object,
wherein the feature values include one or more of a root-mean square of an amplitude of the detected portion of the waves, a variance of the amplitude of the detected portion of the waves, a cross-correlation value of the amplitude of the detected portion of the waves, an auto-correlation value of the amplitude of the detected portion of the waves, a peak-to-peak value of the amplitude of the detected portion of the waves, a peak value of the amplitude of the detected portion of the waves, a Kurtosis value of the amplitude of the detected portion of the waves, a time-domain statistical moment corresponding to properties of the detected portion of the waves, a frequency-domain statistical moment corresponding to the properties of the detected portion of the waves, and one or more normalized values of one or more of the feature values, and wherein the waves are produced by applying energy to the object at an application point.

26. The non-transitory computer-program product of claim 25, wherein the instructions that cause the processor-based device to compute the one or more variation values comprise instructions that cause the processor-based device to at least:

compute a value based on the equation:

$$\text{Mahalanobis Squared Distance (M.S.D.)} = (x-\bar{x})^T \times Cov^{-1} \times (x-\bar{x})$$

where x is a vector of the computed feature values, is the mean vector of the corresponding baseline feature values, represents a covariance matrix operation, T represents a transpose operation and −1 represents an inverse matrix operation.

27. The non-transitory computer program product of claim 25, wherein the instructions further comprise instructions to cause the processor-based device to at least:

cause the energy to be applied to the object to cause acoustic bulk waves, including one or more of longitudinal waves and shear waves, to travel through the object at specified angles to enhance the defect detection sensitivity.

28. A system comprising:

at least one generator configured to apply energy to an object at an application point to cause waves to travel, at least partly, through the object;

at least one detector configured to detect at least a portion of the waves traveling through the object, wherein the at least one detector includes two or more acoustic detectors positioned at one of different sides of the application point or on the same side of the application point, and wherein the two or more acoustic detectors are configured to detect guided waves portions resulting from the energy applied to the object, the guided waves portions traveling at a direction substantially parallel to the longitudinal axis of the object; and a statistical analyzer configured to perform a statistical analysis based on an output produced by the at least one detector in response to the detected portion of the waves, the statistical analysis being used to determine whether at least one defect is present in the object.

29. The system of claim 28, wherein the statistical analyzer is configured to at least:

determine one or more variation values between features of the respective portions of the guided waves detected by the two or more detectors.

30. The system of claim 29, wherein the statistical analyzer is configured to at least:

compute ratio values of the features of the respective detected portions of the guided waves.

31. A method comprising:

applying, by at least one generator, energy to an object at an application point to cause waves to travel, at least partly, through the object;

detecting, by at least one detector, at least a portion of the waves traveling through the object, wherein the at least one detector includes two or more acoustic detectors positioned at one of different sides of the application point or on the same side of the application point, and wherein the two or more acoustic detectors are configured to detect guided waves portions resulting from the energy applied to the object, the guided waves portions traveling at a direction substantially parallel to the longitudinal axis of the object; and performing, by a statistical analyzer, a statistical analysis based on an output produced by the at least one detector in response to the detected portion of the waves, the statistical analysis being used to determine whether at least one defect is present in the object.

32. A non-transitory computer program product residing on a computer readable medium and comprising computer instructions that when executed on a processor-based device cause the processor-based device to at least:

apply energy to an object at an application point to cause waves to travel, at least partly, through the object;

detect at least a portion of the waves traveling through the object, wherein the at least one detector includes two or more acoustic detectors positioned at one of different sides of the application point or on the same side of the application point, and wherein the two or more acoustic detectors are configured to detect guided waves portions resulting from the energy applied to the object, the guided waves portions traveling at a direction substantially parallel to the longitudinal axis of the object; and perform a statistical analysis based on an output produced by the at least one detector in response to the detected portion of the waves, the statistical analysis being used to determine whether at least one defect is present in the object.

* * * * *